United States Patent [19]

Kitchell et al.

[11] Patent Number: 4,692,328
[45] Date of Patent: Sep. 8, 1987

[54] BIOLOGICALLY USEFUL POLYMER PREPARATIONS

[75] Inventors: Judith P. Kitchell, Newton, Mass.; Stanton R. de Riel, Pembroke Pines, Fla.

[73] Assignee: Dynatech Corporation, Cambridge, Mass.

[21] Appl. No.: 780,162

[22] Filed: Sep. 24, 1985

[51] Int. Cl.$^4$ ............................................. A61K 31/74
[52] U.S. Cl. ...................................... 424/78; 424/80; 524/548; 525/161
[58] Field of Search .................... 424/78, 80; 525/161; 524/548

[56] References Cited

U.S. PATENT DOCUMENTS

| | | |
|---|---|---|
| 3,563,968 | 2/1971 | Merijan et al. |
| 3,755,561 | 8/1973 | Raukin .................................. 424/78 |
| 3,954,682 | 5/1976 | Fein et al. ............................. 424/78 |
| 3,954,960 | 5/1976 | Valan .................................... 424/78 |
| 4,057,623 | 11/1977 | Hase et al. ............................ 424/78 |
| 4,273,135 | 6/1981 | Larimore et al. |
| 4,321,263 | 3/1982 | Powell et al. ......................... 424/78 |
| 4,383,529 | 5/1983 | Webster. |
| 4,481,167 | 11/1984 | Ginter et al. ......................... 424/78 |
| 4,482,533 | 11/1984 | Keith ..................................... 424/78 |
| 4,500,339 | 2/1985 | Young et al. ......................... 424/78 |
| 4,504,582 | 3/1985 | Swann .................................. 424/78 |
| 4,554,155 | 11/1985 | Allan et al. ........................... 424/78 |

OTHER PUBLICATIONS

Glass, James M., et al, *The Quantity and Distribution of Radiolabeled Dexamethasone Delivered to Tissue by Iontophoresis*, vol. 19, pp. 519–525, (1980).

Noyes Data Corporation, *Water–Soluble Polymers, Technology and Applications*, (1972), By Yale L. Meltzer.

Waud, D. R., *Iontophoretic Application of Drugs*, pp. 128–130, (1967).

Russo, John Jr., et al, *Lidocain Anesthesia: Comparison of Iontophoresis, Injection and Swabbing*, pp. 843–847, (1980).

J. Biomed. Mater. Res., *Evaluation of Wound–Covering Materials*, vol. 11, pp. 489–502, (1977).

Motion Control, Iontophoresis—*The Non-Invasive Administration of Drugs*, (Brochure).

CRC Press Inc., *Burn Wound Coverings*, vol. II, pp. 125–155.

Primary Examiner—Joseph L. Schofer
Assistant Examiner—Bernard Lipman
Attorney, Agent, or Firm—Cesari and McKenna

[57] ABSTRACT

Described and claimed are biologically useful crosslinked copolymers of vinyl pyrrolidone and allylamine suitable for various preventative and therapeutic applications to intact or injured skin. Coatings of these copolymers, either preformed or prepared in situ on the skin may deliver medicaments to the skin, may serve as an iontophoretic medium, may provide electrical contact with the body, may regulate or control moisture loss from injured integument. Monolithic devices for the delivery of pharmaceutically active agents within living tissue may be formulated from these copolymers.

6 Claims, No Drawings

BIOLOGICALLY USEFUL POLYMER PREPARATIONS

STATEMENT OF GOVERNMENT INTEREST

The invention described herein was made with Government support under Contract N00014-81-C-0468 awarded by the Department of the Navy, and may be manufactured and used by or for the Government of the United States of America for Governmental purposes without the payment of any royalties thereon or therefor.

FIELD OF THE INVENTION

This invention relates to adherent, biocompatible, conforming, polymeric coatings for intact or wounded skin suitable for the delivery to skin of pharmacologically active agents and the effective protection against bacterial invasion, fluid loss and mechanical injury, the polymers of said coatings being useful in the fabrication of monolithic devices for the delivery of drugs.

BACKGROUND OF THE INVENTION

Many occasions arise in which it is desired to apply a covering to the skin for therapeutic purposes. In the case of intact skin it may be desirable to apply a coating which contains a therapeutic agent to be taken up by the skin. A coating on intact skin also may serve to protect an area of skin against physical forces: abrasion or compression, for example. Injured or unhealthy skin requires coverings for therapy and protection, as well. Burns, wounds, ulcers and debilitated areas and skin-graft donor sites benefit from the delivery of therapeutic agents, the exclusion of ambient bacteria, the prevention of water loss, physical protection, and the preclusion of local accumulation of tissue fluids at the skin surface.

Objectives of this kind are met to some degree by bandages, foils or sheet material, either uniform or composite in structure, held in place by tying or adhesives. More intimate contact and easier application is achieved with creams or ointments, but these suffer from impermanence. Dissatisfaction with such skin coverings has stimulated search and invention of improved skin coverings of broad or specific utility. Many kinds of skin coverings suggested or investigated for utility are described by G. B. Park, *Biomat. Med. Dev., Art. Org.* 6 (1) 1–35 (1978). Although some skin covering materials have evolved through intuitive or empirical effort, most modern investigators are guided by recognition that there is need to meet such requirements as repeatable fabrication from available materials of appropriate costs, biocompatibility (including lack of antigenicity), ready conformability to the contours of the skin, adequate physical integrity, compatibility and lack of reactivity with pharmacological agents, regulated properties of water vapor transmission, capable of being rendered sterile or treatable in such a way so as not to constitute a bacterial host, suitable physical properties, e.g., elasticity, abrasion resistance, and strength, adherence to intact or injured skin, and in some instances, more narrowly specified properties. Despite improvements and advances in the technology, ideal or universally applicable systems have not yet been offered.

Although synthetic polymeric substances have played a part in providing materials for skin coverings, shortcomings persist. It will be apparent to those active in the fields of medicine, chemistry, and bioengineering, however, that the opportunity exists to discover polymeric substances meeting the perceived needs. A specially promising area of investigation is the chemical alteration of polymers known already to be biocompatible.

SUMMARY OF THE INVENTION

The polymer poly (N-vinyl-2-pyrrolidinone), commonly known as vinyl pyrrolidone, is well known in medicine and pharmacology and is described in the *United States Pharmacopia* as a linear polymer of varying degrees of polymerization. It is valued for its biological compatibility, low toxicity, and inertness, suiting it for such applications as blood extender, tablet binder, drug complexant, antiseptic carrier, and transdermal drug delivery agent. These characteristics recommend vinyl pyrrolidone as an ingredient for preparing additional polymers for skin coatings. With this objective of preparing a polymer based on vinyl pyrrolidone an investigation was conducted to reveal copolymerizing substances which would render the resulting polymer susceptible to crosslinking in such a way that hydrogels could be readily formed, such hydrogels being required to be conformable and adhere to intact or injured skin and to retain coherence after the loss of some, or all or substantially all of the water contained in the initial gel. We have found that such copolymers can be prepared by reacting vinyl pyrrolidone with allylamine and that useful skin coatings can be prepared by crosslinking such copolymers with dicarbonyl reagents such as glutaraldehyde. Additionally the copolymer of vinyl pyrrolidone and allylamine may be partially crosslinked with an unsaturated aliphatic acid halide, e.g., fumaryl chloride, before further crosslinking with dicarbonyl reagent such as glutaraldehyde to provide a gel and coating of similar utility. Still further, the copolymer of vinyl pyrrolidone and allylamine may be degraded by reaction with acid vapor such as hydrochloric acid and the product reacted with an unsaturated aliphatic acid halide, e.g., fumaryl chloride, to produce a substance which can be crosslinked with vinyl pyrrolidone in the presence of a free radical generating catalyst of the peroxide family.

Aqueous gels of such crosslinked polymers may be prepared in situ on skin or fabricated separately and applied as an already existing, pliant film to skin.

Accordingly an objective of the application of such polymeric preparations as coatings to intact or injured skin is to provide protection against abrasion (as in athletic activity), to prevent water vapor loss from injured or burned skin surface, or to protect against bacterial invasion.

Another objective is to deliver pharmaceutically active agents from such coatings either directly to injured skin surface, or transdermally by diffusion from such coating through the skin, or under the influence of an electric field, that is, iontophoretically, through the skin.

Still another objective is to provide an electrode material for making effective electrical connections to the skin.

A further objective is to prepare monolithic structures of the polymers described containing active agents and intended as sustained release sources of such agents, for example, in the form of a bolus to be administered to cattle.

DESCRIPTION OF THE PREFERRED EMBODIMENT

Polymeric skin coatings according to the invention are prepared by the co-polymerization of N-vinylpyrrolidone and allylamine and subjecting the resulting copolymer (designated as PViPAA) to more or less cross-linking through reaction at the amine groups contributed to the structure by the allylamine. Because coatings and films of such cross-linked polymers are brittle in the absence of solvent it is desirable to add a plasticizing agent to the polymer. It has been found beneficial, in addition, to incorporate a proportion of surface active agent in the polymer. Such surfactant addition was observed to enhance the spreadability of polymer gels.

The copolymerization of N-vinylpyrrolidone and allylamine is a reaction already known in the polymer art, as described, for example, by Merijan, Barabas and Fein, U.S. Pat. No. 3,563,968. Such co-polymerization involves the reaction of N-vinylpyrrolidone with an α-olefinic amine in an inert solvent in the presence of a peroxide catalyst. This patent states that polymers may be prepared in this way from a variety of α-olefinic amines, a number of peroxides and hydroperoxides, and an assortment of inert solvents, e.g., alcohols, glycols and ethers.

As an example of a useful polymer of this kind for the practice of our invention there may be cited the polymer prepared by the mixture of 4 volumes of N-vinylpyrrolidone, 0.12 volume allylamine, 0.03 volume t-butyl peroxybenzoate, and, 6 volumes of ethanol. This mixture was held in a closed borosilicate glass vessel at 80° C. for 18 hours. Prior to commencing the reaction the air in the space over the liquid in the vessel was displaced with nitrogen gas. The product was a viscous yellow mass. To this mass was added sufficient methylene chloride to make a fluid pourable at room temperature. This solution was added dropwise to a tenfold volume of ethyl ether. The resulting precipitate was recovered by vacuum filtration on Whatman No. 42 filter paper supported in a Buchner funnel. The recovered polymer was dried at 30° C. by exposure to vacuum overnight. The product was a powder of white, or light tan color.

We have have investigated the properties of polymers prepared with other catalysts, namely, hydrogen peroxide, other peroxides, hydroperoxides, peroxyesters, peroxysulfates and azo compounds. It was judged that t-butyl peroxybenzoate provides the most satisfactory catalyst. We have observed the character of polymers prepared with different proportions of allylamine and t-butyl peroxybenzoate. Specifically, polymers were prepared with ranges of these ingredients as summarized in Table I.

TABLE I

| Ingredient | Weight Percent of Ingredient | |
|---|---|---|
| | Series I | Series II |
| Vinylpyrrolidone | 40 | 40 |
| Allylamine | 0–4.0% | 1.2 |
| t-butylperoxybenzoate | 0.1 | 0.03–3.0 |
| Ethanol | balance | balance |
| Total | 100 | 100 |

In order to characterize such polymers quantitatively the molecular weight distribution of two representative polymers was determined by gel permeation chromatography (GPC) with a reference to polystyrene standards. The results of these GPC measurements are summarized in Table II.

TABLE II

| | Batch A | Batch B |
|---|---|---|
| COMPOSITION (Volumes of Reactant) | | |
| Vinylpyrrolidone | 4 | 4 |
| Allylamine | 0.12 | 0.12 |
| t-butylperoxybenzoate | 0.3 | 0.03 |
| Ethanol | 6 | 6 |
| MOLECULAR WEIGHT MAXIMA (Associated area of GPC Curve, %) | | |
| Peak 1 | 9,300 (83) | 27,700 (73) |
| Peak 2 | Obscured | 2,700 (22) |
| Peak 3 | 900 (17) | 1,500 (5) |

These measurements indicate that three polymeric fractions are present in polymer prepared as described. It was observed that the polymer of molecular weight near Peak 2 was of opposite refractive polarity relative to the elute, dimethyl formamide to the polarities of polymer near Peaks 1 and 3.

The practical utility of our invention is achieved by preparing coherent coatings of the described polymers by suitable chemical crosslinking of the polymer structure. The polymers described are soluble in water at room temperature. However, even concentrated aqueous solutions of such copolymers of vinylpyrrolidone and allylamine are not sufficiently viscous and coherent to form useful coatings on the skin. Furthermore, upon drying, such solutions revert to the powder from which the solution was derived. We have found that a coherent coating of utility may be formed by crosslinking the copolymers of vinylpyrrolidone and allylamine.

We have found that glutaraldehyde is an effective crosslinking agent for PViPAA. The addition of dilute aqueous solution of glutaraldehyde to an aqueous or alcohol solution of PViPAA produces a gel more or less rapidly according to the molecular weight of the PViPAA and its concentration in the solution. The effect of the concentration of polymer on gel formation at a fixed final glutaraldehyde concentration (3.6%) was studied using the polymers designated Batch A and Batch B in Table II. Aqueous solutions were prepared of these polymers ranging from 10 to 60 percent polymer on a weight/volume basis, that is, 100×weight polymer (grams)÷volume solvent (milliliters)=% (wt/vol). Working at room temperature, 0.5 ml of 25% (wt/vol) glutaraldehyde was added to 3 ml aqueous PViPAA solution to give a final concentration of 3.6% glutaraldehyde in solution and the consistency of the resulting mixture was observed for 5 minutes. These observations are summarized in Table III.

TABLE III

| PViPAA Concentration, | Speed, Nature Of Gelation | |
|---|---|---|
| % (wt/vol) | Batch A | Batch B |
| 10 | None | None |
| 20 | None | Moderate |
| 30 | None | Rapid, Firm |
| 40 | Mild | Rapid, Firm |
| 50 | Moderate | Rapid, Firm |
| 60 | Rapid, Firm | Rapid, Firm |

Similar experiments with a solution of 20% (wt/vol) aqueous Batch B at pH 9.2 established that with 1% final concentration glutaraldehyde, gelation was immediate; use of 0.4% glutaraldehyde gave set up in 30 seconds. Addition of 0.2% glutaraldehyde gave a weak gel in several minutes. Using 40% solution of Batch B and 0.16% glutaraldehyde, an immediate, progressively firming gel developed. When the amount of glutaraldehyde was decreased to 0.04%, soft gel was formed. At pH 6.6, gelation was slower than at pH 9, but the final firmness was unaffected. At pH 2, no gelation took place, but as pH was raised with NaHCO$_3$, a uniform, foamy gel formed. These experiments delineated a useful range of conditions for cross-linking with glutaraldehyde.

Since unreacted glutaraldehyde may act as an irritant in some instances, it may be desirable to leach unreacted glutaraldehyde from coatings after crosslinking. In cases where the coating is formed separately (either unsupported or reinforced with fibers, gauze, or the like) before application to the skin, the separately formed coating may be leached in water. In instances where the coating is applied directly to the skin as a still-reacting or just-reacted gel, the coated part may be soaked in water or the coating may be sponged gently to remove excess glutaraldehyde.

Additionally we have discovered that PViPAA may be modified by reaction with fumaryl chloride, $C_4H_2O_2Cl_2$, to provide a substance well suited to preparing skin coatings of the kind desired. Samples of PViPAA, slightly crosslinked with fumaryl chloride (designated PViPAA-F), were prepared as follows. PViPAA polymer was prepared by reacting 4 volumes of redistilled N-vinylpyrrolidone, 0.12 volumes allylamine, 0.02 volumes of t-butylperoxybenzoate, and 2.66 volumes of ethanol at 70° C. under a nitrogen atmosphere for 43 hours followed by precipitation into ethyl ether from methylene chloride solution and vacuum drying. To a solution of 2.00 g PViPAA and 10 drops triethylamine in 40 ml of methylene chloride in a flask was added dropwise and with stirring 2.00 ml of 0.051% wt/wt fumaryl chloride in methylene chloride solution. Half the product was reserved, and an additional 1.00 ml of the fumaryl chloride solution added to the remaining PViPAA solution. The PViPAA was precipitated by adding each product solution dropwise to 300 ml of stirred anhydrous ethyl ether, filtered, washed with 50 ml dry ethyl ether, and vacuum-dried 18 hours at room temperature. The products, thus crosslinked at levels of fumaryl chloride: PV;PAA of 0.5: and 1.0:1000 (wt/wt), (net weights 0.76 and 0.88 g) were then tested for gelation properties.

The test for gelation properties was run in the following way: 30 wt % solutions of parent PViPAA, and the two cross-linked materials were prepared in 0.005M pH 7 phosphate buffer (Fisher) and the pH measured to be 7.89, 7.88, and 7.64, respectively. The fumaryl crosslinked-PViPAA solutions were very slightly more viscous than the control, and slightly hazy, as opposed to clear, yellow. These polymer solutions were all mixed with water and 1.2% (wt/vol) aqueous glutaraldehyde solution so as to give a final polymer concentration of 20% and a series of final glutaraldehyde concentrations of 0.4, 0.2, 0.15, 0.10, 0.08 and 0.06% (wt/vol) in separate vessels. Gelation was almost instantaneous at 0.4% glutaraldehyde, ≦45 sec @0.2%, ≦1 min 40 sec @0.15%, ≦3 min 15 sec @0.10%, and ≦4 min 45 sec @0.08%. At concentrations of 0.15% or less, the firmness of the gel formed increased with increasing cross-linkage of PViPAA. At the 0.06% glutaraldehyde concentration, the fumaryl crosslinked PViPAA samples formed soft and medium gels, respectively, by 6 minutes; the uncrosslinked-PViPAA took until 8 minutes to become stringy, and did not set further (remained liquid beyond 15 minutes). These results confirm the feasibility of using this method of pre-crosslinking to easily and controllably enable the use of lesser amounts of glutaraldehyde in the gel formulation.

As an alternative to the use of glutaraldehyde as cross-linking agent compositions were developed suitable for radical initiated crosslinking through fumaryl moieties in the structure. We have found that a derivatized PViPAA (designated PViPAA-FF) may be prepared by taking a degraded, partially acid hydrolysed PViPAA, extensively reacting it with fumaryl chloride and recovering the polymer, which now has many pendant or linking groups containing the carbon-carbon double bonds of the fumaryl moiety. Thus PViPAA like that used to prepare PViPAA-F was dissolved in methylene chloride/ethanol solution, and hydrogen chloride gas bubbled through. A precipitate formed, which was redissolved by warming in ethanol; the solution was added to ethyl ether to precipitate the degraded, partially hydrolyzed PViPAA. This product, which was quite acidic (pH ~2@10% in $H_2O$), was quite inferior at gelation with glutaraldehyde, forming only a very weak gel at 15% concentration under the same conditions that the parent PViPAA formed a weak gel at 9.5% concentration. However, it now had many more sites for reaction with fumaryl chloride. This product was dissolved as a 10% solution in methylene chloride and 2% fumaryl chloride, to a total of 1:60 wt/wt fumaryl chloride:PViPAA, added, with tertiary amine present to buffer. The polymer was precipitated into ethyl ether and dried, and will be referred to as extensively fumarylated PViPAA, or PViPAA-FF.

PViPAA-FF may be converted to a gel through admixture with hydrogen peroxide and vinyl pyrrolidone monomer. For example, proportions of one part by weight PViPAA-FF, 0.022 part by weight 30 wt. % hydrogen peroxide, one-half ml vinyl pyrrolidone, and one-half ml water formed a soft gel after exposure to 37° C. for one hour. A firm gel resulted after 45 minutes of 37° C. exposure of a mixture of one part by weight PViPAA-FF, 0.36 part 30 wt. % hydrogen peroxide, 0.83 ml vinyl pyrrolidone, and 2.5 ml water. These gels are suitable for skin coatings.

Formulations of PViPAA-FF also have been found to have utility in the preparation of monolithic structures as in the manufacture of boluses suitable for the delivery of beneficial substances to the rumen of cattle. Demonstrations of bolus preparation were carried out by curing the compositions summarized in Table IV. All of the samples prepared according to the formulas of Table IV maintained integrity after immersion for 3 days in water. Sample 3 remained firm, sample 2 was slightly less firm, and sample 1 was deformable.

TABLE IV

| Ingredient | Parts By Weight | | |
|---|---|---|---|
| | Sample 1 | Sample 2 | Sample 3 |
| PViPAA-FF | 1 | 1 | 1 |
| Vinyl pyrrolidone | 0.38 | 0.38 | 0.38 |
| Catalyst | Benzoyl peroxide | 30% Aqueous Hydrogen Peroxide | |
| Amount | 0.12 | 0.09 | 0.09 |
| Filler | None | $CaSO_4.2H_2O$-240 mesh Silica | |
| Amount | 0 | 2.5 | 2.5 |

The foregoing demonstrate the formulations of PViPPA, PViPPA-F, and PViPPA-FF polymers. To improve the functionality and utility of the coatings composed of these materials, we have investigated the characteristics of these coatings with certain additives, such as plasticizers and surfactants, and under different pHs.

We have tested glycerol, triacetin, di(2-methoxy ethyl)phthalate, polyethylene glycol 3350, polyglycol E400, 1,3-butyleneglycol, and polyvinylalcohol as plasticizers with PViPPA. In each case, 7% plasticizer (vol/vol final) was used with 20% polymer and 0.17% glutaraldehyde (pH 5.9). The solution was cast onto a glass plate as a 0.020 in. film. At this pH, gelation requires ≧10 minutes on all films or in bulk. Of these plasticizers, the phthalate and triacetin blush out and are unsuitable. Polyvinylalcohol forms a hard, brittle film quite resistant to solubilizing by $H_2O$; the butyleneglycol forms a slightly tacky gel, which eventually loses plasticity; glycerol and the polyglycol plasticize effectively and do not dry out; whereas an unplasticized gel film dries to brittleness.

Bipcompatibility consideration of polyglycol vs. glycerol favors the latter as a plasticizer for wound-covering applications. The usable proportion of glycerol was determined to be between 0.35 and 0.45 grams anhydrous glycerol/per gram PViPAA solids like that of Batch B of Table II. The optimal ratio was 0.38:1. This film is pliable and relatively tough.

We have found that further beneficial modification of PViPAA films is provided by incorporation of a surface active agent. The presence of surfactant was observed to aid in the wetting of surfaces by gels of PViPAA. The surfactants and sodium lauryl (dodecyl) sulfate have been found effective in this manner. A proportion of surfactant of 0.3% (wt/wt) of the PViPAA solids was found useful for this purpose.

Since these materials are to be applied to living tissue it is desirable that the solutions and gels of PViPAA have neutral or near-neutral pH. When formulations of PViPAA with various ingredients are prepared it may be desirable to adjust the pH. For example, a preparation found to be undesirably alkaline may be made acceptable by the addition of dilute acid such as 1 normal hydrochloric acid. An effective way to control the pH of these preparations is to use an aqueous buffer solution in the preparation. Such a buffer solution may be prepared by dissolving 0.84 grams $NA_2HPO_4$, 0.56 grams $NAH_2PO_4.H_2O$, and 0.1 gram sodium lauryl sulfate in 100 ml distilled water. When 13.1 grams PViPAA of the same composition cited above in the preparation of PViPAA-F was dissolved in 30.6 grams of this buffer solution the resulting pH was measured to be 7.2, whereas an unbuffered solution of PViPAA was found to have a pH of about 8.5.

Having demonstrated various formulations of these skin coatings, evidence of their functional quality and performance were then evaluated. The rate of transmission of water vapor through a skin coating is an important attribute. The permeability of films of the subject invention was measured in experiments carried out with a Fisher Permeability Cup, catalog No. 13-338, manufactured by Fisher Scientific Division, Allied Chemical Corp. PViPAA films of different thicknesses were prepared by mixing in the following sequence: 11.7 grams PViPAA of the composition of Batch B in Table II, 14.5 grams methanol, 9.2 ml 50% aqueous glycerol, 0.035 grams sodium dodecyl sulfate, and 23 drops/ of one normal hydrochloric acid (which resulted in a pH of 6.0), and 0.8 ml per 5 grams of the foregoing ingredients of 3.5% (wt/volume) aqueous glutaraldehyde. Different quantities of this mixture were poured quickly after mixing into Petri dishes. Following gelation and drying overnight at 20° C. in air, these films were clamped into position in Fisher Permeability Cups over distilled water. The cups were maintained in still air at 37° C. for 144 hours. The weight loss (due to pervaporation) of the cups was measured daily. After daily measurement, the films were unclamped, lifted, and reseated to relieve inpouching which otherwise occurred due to much greater permeability of the films to water vapor than to air. More distilled water was added if necessary at this time to maintain water level in the cup near 10 ml. Films were then reclamped, reweighed, and replaced in the measurement chamber. At a time 27 hours after commencement of the test the thickness of the films was measured directly. The cumulative loss of water by pervaporation through these films in these tests was found to progress linearly with time. The data observed are summarized in Table V. As a basis for comparison the rate of water loss from a test cup without a film present was measured to be 0.04–0.05 $g/hr.cm^2$. The data of Table V indicate that pervaporation rate is inversely proportional to film thickness. This relationship may be used to determine what film thickness is required to obtain a film of a given pervaporation rate.

TABLE V

|  | Sample 1 | Sample 2 | Sample 3 |
|---|---|---|---|
| Dry Film, Weight per Unit Area, $g/cm^2$ | 0.030 | 0.055 | 0.092 |
| Hydrated Film Thickness, cm | 0.033 | 0.063 | 0.099 |
| Pervaporation Rate, Average, $g/hr\ cm^2$ | 0.013 | 0.010 | 0.008 |

The potential for drug delivery from these skin coatings was determined by measuring the rate of extraction of sulfadiazine and penicillin-G into water from films containing these agents. In this demonstration polyethylene glycol of molecular weight 3350 (PEG-3350) was chosen as plasticizer, and its effect on drug extraction was observed by incorporating it at two levels and omitting it. PViPAA of the same composition cited above in the preparation of PViPAA-F was combined with sulfadiazine or sodium benzyl penicillin, plasticizer, water and cross-linking reagent plus distilled water to make samples containing the quantities summarized in Table VI. The resulting solutions contained about 2% penicillin and 8% sulfadiazine, respectively.

TABLE VI

|  | Antibacterial Agent | |
|---|---|---|
| Film Ingredients | 200 mg Sulfadiazine | 50 mg Penicillin G |
| PViPAA, mg | 600 | 600 |
| PEG-3350, mg | 0–600 | 0–600 |
| Water | Sufficient to make 2.4 g with above | |
| 2.5% Aqueous Glutaraldehyde, ml | 0.25 | 0.25 |

Immediately after thorough mixing the quantities indicated were poured into 250 ml Erlenmeyer flasks so as to coat the flask bottom of about 38 $cm^2$ area (by difference it was determined that 76% to 92% of the individual samples were transferred to the Erlenmeyer flasks). After 25 min–2 ½ hr of setting time, leaching was started by adding 200 ml of warm leaching medium to each flask, consisting of 0.05M $KH_2PO_4$/NaOH pH 7.00 (25° C.) buffer (Fisher Scientific). The flasks were placed in a constant temperature room and the concentration of extracted antibacterial agent determined by ultraviolet absorption spectroscopy. Temperatures and absorption wavelengths were, respectively: penicillin, 37° C. and 259 nm; sulfadiazine, 34° and 273 nm. The resulting data showed that incorporation of these relatively soluble drugs in the PViPAA hydrogel did restrain and regulate their delivery into the aqueous leaching medium. The presence or absence of the plasticizer, PEG-3350, did not affect the rate of leaching. The penicillin was virtually completely leached from these films after 18 hours. The sulfadiazine, a less soluble drug, was removed from the films after 94 hours exposure, that is, about 4 days. In both instances the extraction of the drug into the surrounding aqueous medium was regular. These experiments demonstrate the utility of PViPAA films in acting as sustained release reservoirs of pharmaceutical or other active agents.

Although qualitative observations of the adherence of PViPAA films to unbroken human skin indicated acceptable adherence, it was of concern to determine quantitatively how well such preparations adhere to skin. A subsidiary concern was the possible influence of drug content in the films on adherence. For this test films were prepared according to the formulas of Table VII, using PViPAA like that of Batch B in Table II. These formulations were applied to the back of a shaved and depilated rat.

TABLE VII

| Ingredient | Quantity, grams | |
|---|---|---|
|  | Sample A | Sample B |
| PViPAA | 5.85 | 5.85 |
| Glycerol | 2.30 | 2.30 |
| Methanol | 7.25 | 7.25 |
| Sodium Dodecyl sulfate | 0.01857 | 0.01857 |
| Glutaraldehyde | 0.099 | 0.099 |
| Distilled Water | 4.95 | 4.95 |
| Penicillin G | 1.47 | 0 |
| Sulfadiazine | 0 | 1.06 |

The formulation containing penicillin was painted on the right side of the rat's back, the one containing sulfadiazine on the left. A gauze bandage, 1 inch wide, was pressed into the wipe-on before crosslinking and then more wipe-on was applied to the gauze to make sure that it was fully imbedded. The rat was anesthetized with ether prior to measuring adherence at 52 hours post-application. Adherence was measured on an Instron Tensile Tester according to a method like that described by Schwope and co-workers, *J. Biomed. Mater. Res.* 11, 489–502 (1977). In all cases the gauze impregnated films were removed intact leaving no film on the rat's backs.

Adherence was calculated from the equation:
Adherence (lbs/in) = AS/LW where:
A = Area under curve (in$^2$)
S = Scale (lbs/in)
L = Length of Area (in)
W = Wound Covering Width (in)

It was found that Sample A, containing penicillin exhibited an adherence of 0.18 lb/in, and Sample B showed 0.28 lb/in. These values were judged to indicate useful levels of adherence.

The skin coatings and hydrogels disclosed herein have additional utility as media for the delivery to and through the skin by the process of iontophoresis. The phenomenon of iontophoresis is the driving of active agents into and through intact skin under the influence of an electric potential. In early practice of this procedure the active agents were incorporated in absorbent pads of material such as gauze, placed on the skin under suitable electrodes. In U.S. Pat. No. 4,383,529 Webster teaches the use of hydrogels as drug reservoirs in iontophoresis. We have found that a hydrogel of PViPAA serves well in this function. In a demonstration, films were prepared from one gram of PViPAA, 1.5 g methanol, 7.5 or 15 mg benzocaine, 1.2 ml glycerol, and 0.4 ml glutaraldehyde. Gel films of this kind were adhered first to an aluminum foil and then, on the side opposite to the foil, to a hydrated nitrocellulose membrane. Two such circular patches of 10 mm diameter were placed at a distance of 4 cm from each other, center to center, on the underside of a membrane supporting 200 ml of 10 millimolar phosphate buffer solution. The patches were connected electrically to the leads of an iontophoretic current source tradenamed The Phoresor and manufactured by Motion Control, Inc., 1005 South 300 West, Salt Lake City, Utah. Current levels of 0, 1.5, and 3 milliamps were generated in separate tests. Samples of the buffer solution were removed periodically and analyzed for benzocaine content by ultraviolet spectrophotometry at 278 nm. Some drug entered the pool of buffer solution at zero current. This represents diffusional transport alone. The amount of drug entering the buffer when current was passed was observed to exceed that entering by diffusion alone by as much as threefold. This simulation of the transdermal transport of benzocaine from a PViPAA electrode provides quantitative demonstration of the utility of PViPAA for this purpose.

In another electrode application, films of PViPAA laden with electrolytes may serve as connectors or coupling interfaces between the skin and an electrical recording device, such as an electrocardiograph. The conductive quality of PViPAA films at modest electrolyte loading was demonstrated in the iontophoresis experiment, but it was of concern to determine whether gels of PViPAA will withstand the presence of substantial loadings of electrolyte, consistent with high levels of electrical conductivity. Samples of 20% PViPAA/H$_2$O were loaded with sodium chloride to the following levels of NaCl:PViPAA solution: 0, 0.5, 1.0, 3.0, 8.9, and 14.0%. Glutaraldehyde was added, to 0.3% of wet weight; final per cent NaCl of the most highly loaded gel was 12.2%. Although the 8 and 14% NaCl additions caused a slight precipitation of PViPAA, upon glutaraldehyde addition all samples gelled identically to soft-medium stage in 12 mins. Thus, these gels demonstrate the ability to tolerate electrolyte loadings and pH changes which would make them suitable as a conductive material applied as a liquid, hardening in a short time to a gel, with further modifications possible by incorporation of plasticizers, wetting agents, or bioactive agents.

Thus, it can be seen from the foregoing that biologically useful, polymeric preparations can be made from copolymers of PViPPA, PViPPA-F, and PViPPA-FF. It is evident that the basic polymer ingredient, namely PViPPA, may be subjected to modifications which alter the susceptibility to crosslinking and gel formation, such as those described in the foregoing disclosure. It is further evident that a variety of crosslinking agents may be utilized.

What is claimed as new and desired to be secured by the Letters Patent of the United States is:

1. A biologically useful polymer preparation prepared by
   A. mixing a first solution comprising 20–60% (weight per volume) copolymer comprising vinyl pyrrolidone and allylamine in a ratio of 10 parts by weight vinyl pyrrolidone to 0-1 part by weight allylamine with a second solution comprising glutaraldehyde to give a final concentration of 0.04–3.6% (weight per volume) glutaraldehyde; and
   B. forming a film from the mixture of step A.

2. A biologically useful polymer preparation according to claim 1 wherein said first solution further comprises 0.05 to 0.1% by weight fumaryl chloride.

3. A biologically useful polymer preparation according to claim 1, wherein said first solution further includes pharmaceutically active agents which will diffuse from the coating to skin covered by the coating.

4. A polymer prepartation according to claim 1 for use as an electrically funcitonal electrode, wherein said first solution further includes electrolytes to provide electrical conductivity.

5. A biologically useful polymer preparation according to claim 1, effective in the regulation of mositure loss from injured or burned skin, wherein the thickness of said film is related to moisture loss from said film.

6. A polymer preparation according to claim 1 wherein said first solution further includes pharmaceutically active agents which may be delivered from the film through iontophoresis into and through intact or injured skin.

* * * * *